(12) United States Patent
Aliane et al.

(10) Patent No.: US 10,145,812 B2
(45) Date of Patent: Dec. 4, 2018

(54) CAPACITIVE HUMIDITY SENSOR WITH GRAPHENE ELECTRODE

(71) Applicant: COMMISSARIAT À L'ÉNERGIE ATOMIQUE ET AUX ÉNERGIES ALTERNATIVES, Paris (FR)

(72) Inventors: Abdelkader Aliane, Grenoble (FR); Jean-Marie Verilhac, Grenoble (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 752 days.

(21) Appl. No.: 14/402,865

(22) PCT Filed: Jun. 4, 2013

(86) PCT No.: PCT/EP2013/061438
§ 371 (c)(1),
(2) Date: Nov. 21, 2014

(87) PCT Pub. No.: WO2013/182542
PCT Pub. Date: Dec. 12, 2013

(65) Prior Publication Data
US 2015/0153297 A1 Jun. 4, 2015

(30) Foreign Application Priority Data
Jun. 4, 2012 (FR) ...................... 12 55178

(51) Int. Cl.
*G01N 27/22* (2006.01)
(52) U.S. Cl.
CPC ......... *G01N 27/223* (2013.01); *G01N 27/225* (2013.01)
(58) Field of Classification Search
CPC .... G01N 27/223; G01N 27/121; G01N 25/56; G01N 1/24

USPC ..... 73/335.04, 335.03, 335.02, 29.02, 29.01, 73/23.2; 324/664, 689
See application file for complete search history.

(56) References Cited

U.S. PATENT DOCUMENTS

| | | | | |
|---|---|---|---|---|
| 7,104,113 B2 * | 9/2006 | Zribi | ...................... | B82Y 15/00 73/25.05 |
| 7,302,829 B2 * | 12/2007 | Zribi | .................... | G01N 29/036 73/23.2 |
| 2004/0194546 A1 * | 10/2004 | Kanehori | ............. | G01N 27/225 73/335.04 |

FOREIGN PATENT DOCUMENTS

| | | |
|---|---|---|
| EP | 1 434 048 A1 | 6/2004 |
| EP | 2 233 920 A1 | 9/2010 |

OTHER PUBLICATIONS

U.S. Appl. No. 14/803,429, filed Jul. 20, 2015, Aliane.
Fazel Yavari, et al., "Tunable Bandgap in Graphene by the Controlled Adsorption of Water Molecules" Wiley-VCH Verlag GmbH & Co. KGaA, Weinheim, Oct. 20, 2010, pp. 2535-2538.
International Search Report dated Sep. 17, 2013 in PCT/EP2013/061438 Filed Jun. 4, 2013.

(Continued)

*Primary Examiner* — Harshad R Patel
*Assistant Examiner* — Nigel Plumb
(74) *Attorney, Agent, or Firm* — Oblon, McClelland, Maier & Neustadt, L.L.P.

(57) ABSTRACT

A humidity-sensing device and a method of producing the humidity-sensing device. The humidity-sensing device is of capacitive type and includes a dielectric material with low permeability to moisture and an electrode with permeability to moisture greater than that of the dielectric material with which it is in contact.

12 Claims, 7 Drawing Sheets

(56) References Cited

OTHER PUBLICATIONS

French Preliminary Search Report and Written Opinion dated Nov. 6, 2012 in Patent Application No. 1255178 Filed Jun. 4, 2012.

Laszlo Juhasz, et al., "A simple humidity sensor with thin film porous alumina and integrated heating", Procedia Engineering, vol. 5, XP027483762, Jan. 2010, pp. 701-704.

L.I. Belic, et al., "AES, AFM and TEM studies of NiCr thin films for capacitive humidity sensors", Thin Solid Films, vol. 317, No. 1-2, XP004147637, Apr. 1998, pp. 173-177.

Yoshiro Sakai, "Humidity sensors using chemically modified polymeric materials", Sensors and Actuators B, vol. 13-14, No. 1-3, XP026588274, May 1993, pp. 82-85.

R. R. Nair, et al., "Unimpeded permeation of water through helium-leak-tight graphene-based membranes", Science, vol. 335, XP055042954, Jan. 27, 2012, pp. 442-444.

\* cited by examiner

CAPACITIVE HUMIDITY SENSOR WITH GRAPHENE ELECTRODE

TECHNICAL FIELD

The invention relates to the field of capacitive detection or measurement devices, in particular those used for detecting and/or measuring humidity.

It concerns an improved humidity sensing device, suitable for detecting or measuring a low level of humidity and the structure of which makes it possible to make measurements at a high measurement frequency, as well as method for producing such a sensor.

PRIOR ART

The measurement of relative humidity by measuring impedance variation is a frequently used technique.

Among the devices for measuring relative humidity by measuring impedance variation, there are those using sensors of the capacitive type comprising a layer of sensitive dielectric material designed to absorb the surrounding moisture.

In such a sensor, the layer of dielectric material is located between two electrodes, the whole forming a capacitor. When the humidity varies, the quantity of water absorbed by said layer of dielectric material also varies, which causes a modification to the dielectric constant of this layer, and a variation in the capacitance of the capacitor, which is measured. This variation may be great because of the high value of the dielectric constant of water, which is around 80.

The document of JUHASZ L et al "A simple humidity sensor with thin film porous alumina and heating", Elsevier Vol. 5, 2010 presents for example a humidity sensor in which the moisture is housed in a layer of alumina. The detection frequency of such a sensor is limited by the drying time of this alumina layer.

The drying of the sensor may in fact pose a problem and prevent the performance of a plurality of consecutive measurements close together.

The problem is posed of finding a novel humidity sensor with improved sensitivity and designed for detecting a low level of humidity.

DISCLOSURE OF THE INVENTION

The invention concerns the production of a device for detecting and/or measuring humidity, provided with a capacitive sensor with improved sensitivity.

For this purpose, the invention proposes a sensor of the capacitive type comprising a top electrode formed by at least one layer based on a given conductive material permeable to moisture, and in contact with a dielectric region with a permeability lower than that of the layer of conductive material.

Thus, according to the invention, a detection of moisture close to the interface between the dielectric region and the layer of given conductive material belonging to the electrode of the sensor is favoured.

In the stack of layers of the sensor, the moisture that is detected is situated on average closer to the outside of the sensor than in the sensors according to the prior art, which makes it possible to achieve better drying, and thus make a larger number of measurements in given period of time than with capacitive sensors with a porous dielectric.

The dielectric region advantageously has low permeability to moisture.

The dielectric region may advantageously be non-porous or have very low porosity, that is to say a maximum degree of porosity of less than 8%.

The dielectric region may in particular be provided with pores having a maximum dimension, also referred to as the diameter, of less than 4 nm.

The dielectric region may also be based on a material having low affinity with water molecules.

The dielectric region may advantageously be hydrophobic.

The dielectric region rests on a bottom electrode of the sensor.

The material of the top electrode may advantageously be graphene. The absorption of water molecules by the graphene modifies its gap.

Graphene is electrically conductive and has sensitivity to humidity, and the presence of water molecules in the graphene may make it semiconductive by increasing its gap.

The top electrode may comprise a layer of graphene formed from several stacked atomic sub-layers.

This layer of graphene may have a thickness of between 100 nm and 5 µm for example.

Water molecules are liable to come to be inserted between atomic sub-layers and thus modify the gap of the material of the top electrode.

Holes passing through the layer forming the top electrode may advantageously be provided in order to improve its permeability to moisture.

These holes may also improve drying.

At least one hole among said holes may also pass through the dielectric material region and reveal the bottom electrode.

The sensor may comprise an alternation of holes revealing the top electrode and holes revealing the bottom electrode.

In order to improve the detection sensitivity, a so-called "self-assembled" hydrophilic monolayer may also be provided on a region, in particular metallic, of the top electrode revealed by a hole formed in said layer of given conductive material and resting on said dielectric region.

In order to improve the detection sensitivity, a so-called "self-assembled" hydrophilic monolayer may also be provided on a region, in particular metallic, of the bottom electrode disclosed by a hole formed in said layer of given conductive material and passing through said dielectric region.

According to one possibility of implementation of the sensor, the top electrode may be covered with a perforated hydrophobic protective layer.

The electrodes of the sensor may be disposed on a flexible support, for example based on a polymer material.

The present invention also concerns a temperature measurement or detection device provided with a sensor as defined above.

According to another aspect, the present invention concerns a method for producing a humidity sensor of the capacitive type, comprising steps consisting of:
- forming on a support at least one conductive layer of a first electrode,
- forming at least one region of dielectric material on said conductive layer of said first electrode,
- forming on said layer of dielectric material a layer of a given conductive material having permeability to moisture greater than that of said region of dielectric material with which it is in contact.

The given material may advantageously be graphene.

The method may comprise, after the formation of the region of dielectric material and prior to the formation of the layer of given conductive material, steps consisting of:

forming a sacrificial masking on the region of dielectric material, then forming at least one metal region on the region of dielectric material through openings in the sacrificial masking revealing the region of dielectric material, removing the sacrificial masking, said layer of given conductive material then being produced around said metallic region with a hole revealing said metallic region.

After the step of removing the sacrificial masking, a step consisting of depositing a hydrophilic SAM layer on the metallic region may be provided.

BRIEF DESCRIPTION OF THE DRAWINGS

The present invention will be understood better from a reading of the description of example embodiments given purely by way of indication and in no way limitatively, referring to the accompanying drawings on which.

Identical, similar or equivalent parts in the various figures bear the same numerical references so as to facilitate passing from one figure to another.

The various parts depicted in the figures are not necessarily shown to a uniform scale, in order to make the figures more legible.

DETAILED DISCLOSURE OF PARTICULAR EMBODIMENTS

Figure 1:
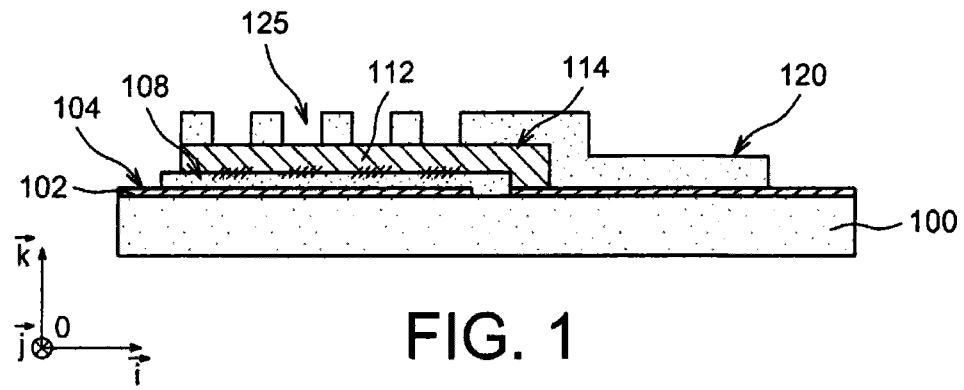
FIG. 1 illustrates a first example of an arrangement of the humidity sensor of the capacitive type, having at least one top electrode permeable to moisture resting on a dielectric region that is not or only slightly permeable to moisture.

An example of a humidity sensor of the capacitive type used according to the invention is given in FIG. 1.

This humidity sensor is formed on a support 100 or a plate 100 which, because of its composition and thickness, may be flexible. The support 100 may be based on a polymer material such as for example PET (polyethylene terephthalate) or PEN (polyethylene naphthalate) or PI (polyimide).

The support 100 may also have a thickness of between 25 μm and 200 μm for example.

The sensor comprises a first electrode 104, also referred to as the "bottom electrode", resting on the support 100, which may be in the form of a conductive layer 102, for example based on metal such as gold or platinum or silver or copper. This conductive layer 102 may have a thickness of between 30 and 300 nanometers for example (the thickness being a dimension measured in a direction parallel to the vector $\vec{k}$ of the orthogonal reference coordinate system [O; $\vec{i}$; $\vec{j}$; $\vec{k}$] defined in FIGS. 1 to 3).

According to another possibility, the conductive layer 102 may be based on graphene.

A layer 102 of graphene disposed on a dielectric material can make it possible to detect the presence of moisture at the grapheme/dielectric material interface, the graphene being able, at this interface, to be semiconductive in contact with $H_2O$ molecules.

A region of dielectric material 108 rests on the first electrode 104. This dielectric material 108 may be a material that is only slightly absorbent of or slightly permeable or even impermeable to moisture.

The dielectric material 108 may be chosen so as not to have any affinity with $H_2O$ molecules, and may optionally be hydrophobic.

The dielectric material 108 may have a weak affinity with moisture and for this purpose may have for example pores with a maximum size or maximum diameter of around 4 nm.

The dielectric material 108 may for example be based on a polymer material such as parylene or polyester, or a polycarbonate or a fluoropolymer of the poly(perfluoro butenyl vinyl ether) type known by the name Cytop® with low relative permittivity $\varepsilon_r$, such that $\varepsilon_r = 2.2$.

The dielectric region 108 may have a thickness of between 100 nm and 2 μm for example.

The region of dielectric material 108 is covered with a second electrode 114 also referred to as the "top electrode" 114. The second electrode 114 is formed from a layer of conductive mater 112, the permeability to moisture of which is higher than that of the dielectric material 108.

This conductive material 112 is advantageously graphene. Conductive graphene may locally, when it is in contact with $H_2O$ molecules, have properties of a semiconductor with a small gap. Such properties are described for example in the document by Yavari et al "Tunable Bandgap in Graphene by the Controlled Absorption of Water Molecules", Wiley-VCH Verlag GmbH & Co.KGaA, Weinheim, 2010.

The layer of conductive material 112 may have a thickness for example of between 100 nm and 5 μm, for example around 1 μm.

The first electrode 104, the dielectric region 108 and the second electrode 114 form a capacitance that is variable according to the humidity.

Because of the moisture-absorbent character of the second electrode 114, and the weakly absorbent or non-absorbent character of the dielectric region 108, the variation in capacitance able to be detected by means of such a sensor depends on a variation in moisture close to the interface between the second electrode 114 and the dielectric region 108.

The second electrode 114 may be covered with a perforated hydrophobic protective dielectric layer 120 comprising openings 125 through which the moisture is intended to enter.

The hydrophobic protective dielectric layer 120 is provided with a thickness of between 1 µm and 15 µm, and preferably greater than 5 µm, in order to avoid the formation of stray capacitance(s).

Figure 2:
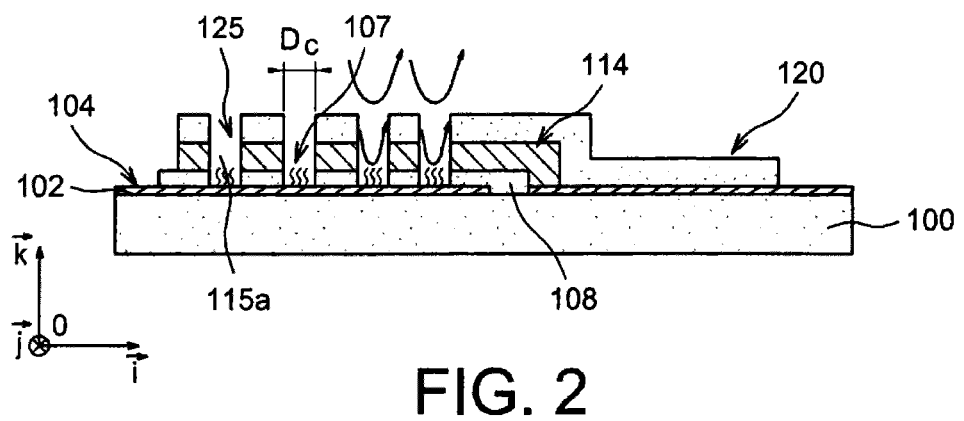
FIG. 2 illustrates a second example of an arrangement of a humidity sensor of the capacitive type according to the invention having at least one top electrode permeable to moisture resting on a dielectric region that is only slightly or not permeable to moisture.

In FIG. 2, another example embodiment of the capacitive humidity sensor according to the invention is given.

In this example, in line with the openings 125 passing through the hydrophobic protective dielectric layer 120, holes 115a are provided passing through the layer of conductive material 112 of the second electrode 114, as well as the dielectric region 108.

These holes 115a serve to trap moisture and also afford drying by convection of the layers 112 and 108 of the sensor that they pass through.

In order to optimise the sensitivity of the humidity sensor, a hydrophilic SAM layer (SAM standing for "self-assembled monolayer") may also be provided at the bottom of the holes 115a on the first electrode 104.

The hydrophilic SAM layer 107 may for example be based on 2,2'-(ethylenedioxy) diethanethiol, or hexa(ethylene glycol) dithiol, or tetra(ethylene glycol) dithiol, or (11-mecaptoundecyl)tetra(ethylene glycol), or (11-mecaptoundecyl)hexa(ethylene glycol), or triethylene glycol mono-11-mercaptoundecyl ether.

The openings 125, and the holes 115a in line with the openings 125, have a critical dimension Dc (measured in a direction parallel to the plane [O; $\vec{i}$; $\vec{j}$] of the orthogonal reference frame [O; $\vec{i}$; $\vec{j}$; $\vec{k}$] defined in FIGS. 1 to 4) which may be between 50 µm and 200 µm, for example around 100 µm.

"Critical dimension" means the smallest dimension of a pattern such as a hole or opening produced in a thin layer apart from its thickness.

Figure 3:
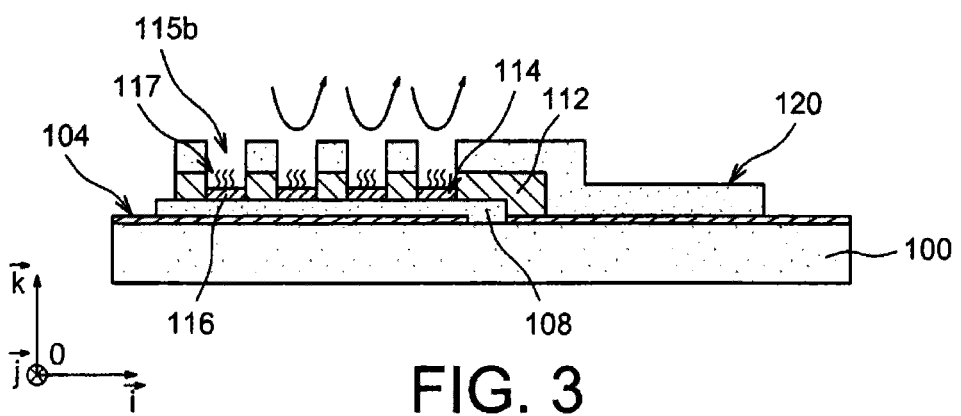
FIG. 3 illustrates a third example of an arrangement of a humidity sensor of the capacitive type according to the invention having at least one top electrode permeable to moisture resting on a dielectric region that is only slightly or not permeable to moisture.

Another example embodiment of the sensor is given in FIG. 3.

In this example, in line with the openings 125 passing through the hydrophobic dielectric layer 120, holes 115b revealing a region formed by a hydrophilic SAM layer 117 are provided, the hydrophilic SAM layer 117 resting on a metallic region 116 of the second electrode 114, itself being disposed on the dielectric region 108 of the capacitor. These holes 115b being used for trapping moisture. The metallic region 116 forms a region of the second electrode 114 resting on the dielectric region 108. The hydrophilic SAM layer 117 improves the sensitivity of the sensor. The holes 115b also allow drying by convection of the layer of conductive material 112.

Figure 4:
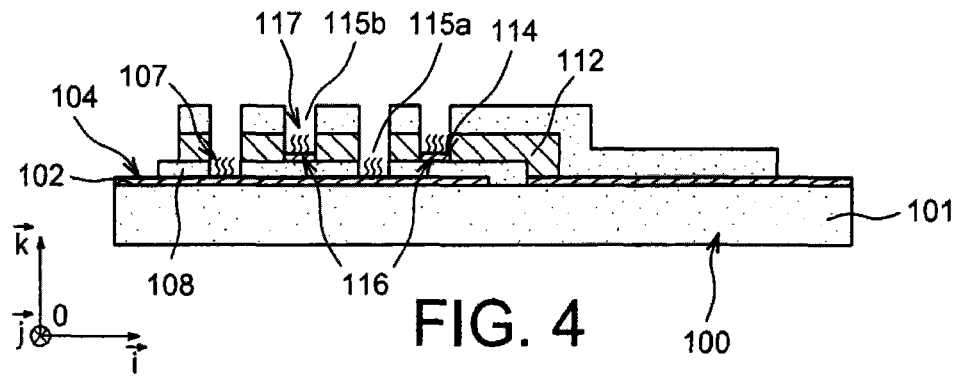
FIG. 4 illustrates a fourth example of an arrangement of a humidity sensor of the capacitive type according to the invention having at least one top electrode permeable to moisture resting on a dielectric region that is only slightly or not permeable to moisture.

Another example embodiment of the sensor is given in FIG. 4.

In this example, the sensor comprises an alternation of holes 115a passing through the layer of conductive material 112 of the second electrode 114 and the dielectric region 108, and other holes 115b passing only through the layer of conductive material 112 of the second electrode 114.

The holes 115a reveal a hydrophilic SAM layer 107, resting on the conductive layer 102 of the first electrode 104.

The other holes 115b for their part reveal a hydrophilic SAM layer 117 resting on a metallic region 116 of the second electrode 114.

Figure 5:
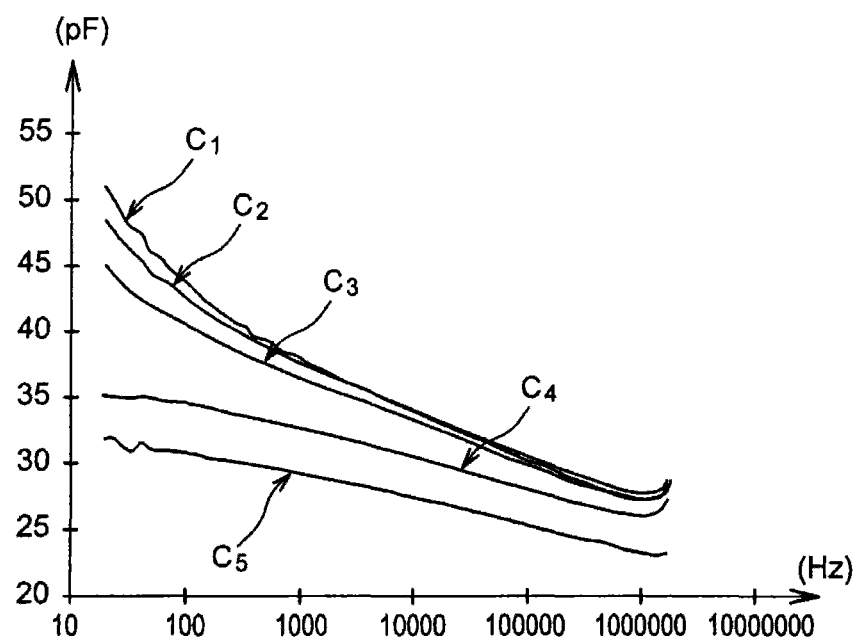
FIGS. 5 and 6 illustrate the results of measurements made by means of a humidity sensor as implemented according to the invention.

FIG. 5 illustrates, by means of curves $C_1$, $C_2$, $C_3$, $C_4$, $C_5$, results of measurements made by means of a humidity sensor comprising a graphene-based electrode. In this example, the detection of the moisture at the graphene-dielectric interface occurs in particular at low frequency. The detection device may be designed to function at very low frequency in order to have maximum sensitivity.

Figure 6:
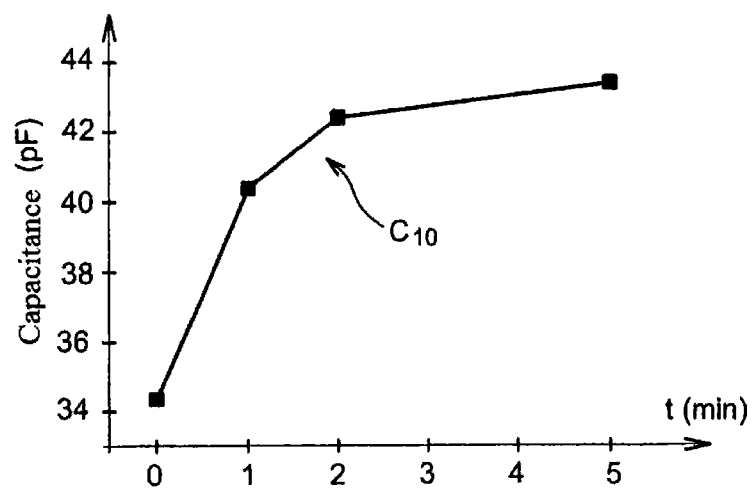

FIG. 6 gives an example of a capacitance-variation curve as a function of time for a sensor used according to the invention having an operating frequency of around 100 Hz.

An example of a method for producing a humidity sensor of the capacitive type according to the invention will now be given in relation to FIGS. 7A to 7D.

The starting material for this method may be a support 100 for example in the form of a substrate based on polymer material, for example based on PEN or PET or PI. The support 100 may also be provided with a thickness of between 25 µm and 200 µm for example and may be flexible.

Next a conductive layer 102 is formed on one face of the support 100. This conductive layer 102 may be based on a metal material, for example based on gold or platinum or nickel or copper or silver or aluminium, and have a thickness of between 30 nm and 300 nm for example, or several micrometers in the case where the conductive layer 112 deposited comprises patterns.

Figure 7A:
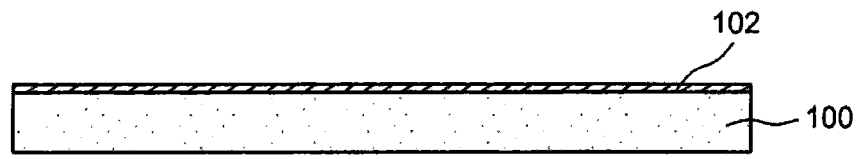
FIGS. 7A to 7D illustrate a first example of a method for producing a humidity sensor of the capacitive type according to the invention.

The conductive layer 102 may be formed by PVD (physical vapour deposition) or by screen printing or by inkjet (FIG. 7A).

Figure 7B:
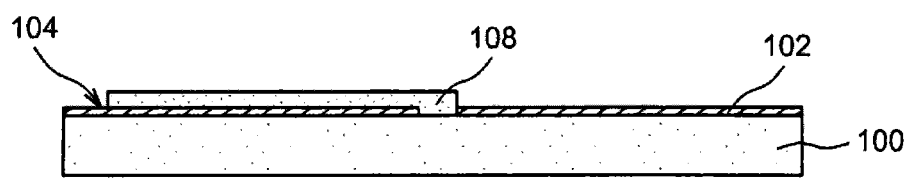

Then, after having etched the conductive layer 102 so as to produce an electrode pattern 104, a layer of dielectric material 108 is formed (FIG. 7B).

This dielectric material may have a low dielectric constant for example such that the relative permittivity $\varepsilon_r$ of this material is between 2 and 3.

The dielectric material 108 is preferably a non-porous material or one provided with pores with a diameter or maximum dimension of less than 4 nm in order to make it only slightly permeable to moisture.

The layer of dielectric material 108 may for example be based on polystyrene or parylene or polyester or polycarbonate or even fluoropolymer of the poly(perfluoro butenyl vinyl ether) type with a low dielectric constant $\varepsilon_r$, for example around 2. The layer of dielectric material 108 may be produced for example by CVD (chemical vapour deposition) or by inkjet or by screen printing, followed optionally by annealing, for example at around 100° C. for around ten minutes for example.

Next another conductive layer 112 is formed on the dielectric region 108 by deposition of a conductive layer 112 permeable to moisture and based on a material the forbidden band of which is able to vary according to the humidity. This conductive material may advantageously be graphene. The conductive layer 112 is intended to form a second electrode 114 of the sensor.

Figure 7C:
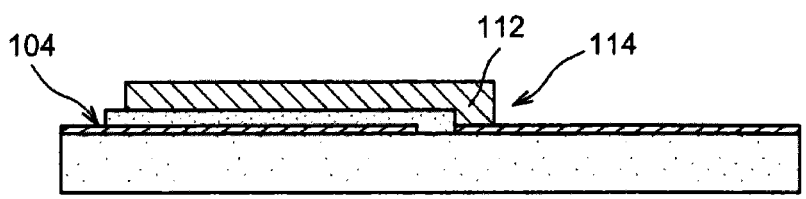

The conductive layer 112 may also have a thickness of between 100 nm and 5 µm for example. The conductive layer 112 may be formed by deposition, or screen printing or inkjet (FIG. 7C).

Then a hydrophobic protective layer 120 is formed on the second electrode 114, for example by screen printing or by inkjet.

This protective layer 120 may be based on a hydrophobic organic polymer material. The hydrophobic protective layer 120 may have a thickness of between 1 µm and 15 µm for example, sufficient to avoid the formation of stray capacitances.

Figure 7D:
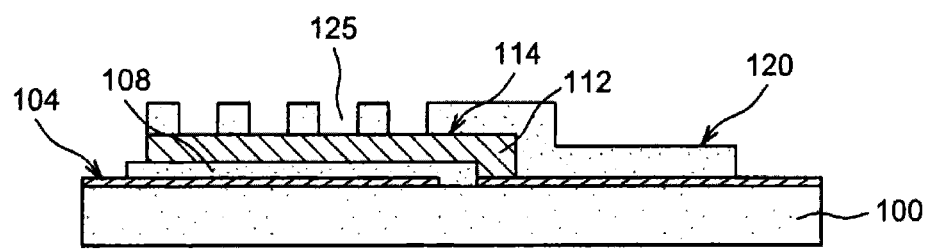

Openings 125 are produced in the layer 120 to allow access to the second electrode 114 (FIG. 7D).

A variant of the example of a method described above will now be given.

Figure 8G:
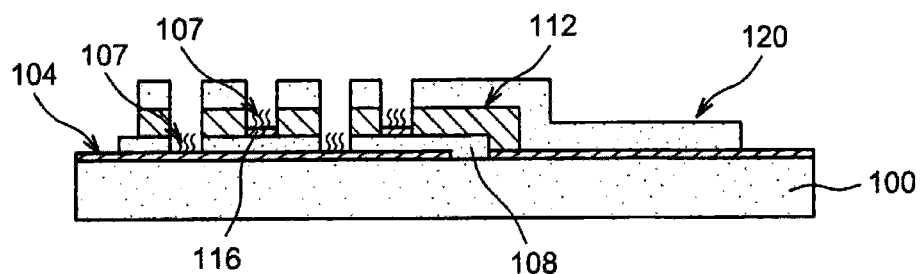
FIGS. 8A to 8G illustrate another example of a method for producing a humidity sensor according to the invention.
Figure 8A:
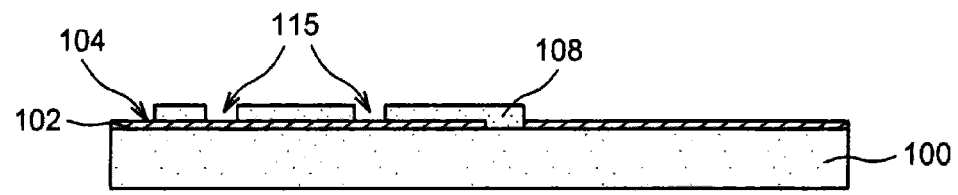

For this variant, holes 115 revealing the conductive layer 102 forming the first electrode 104 are produced in the layer of dielectric material 108 (FIG. 8A).

Figure 8B:
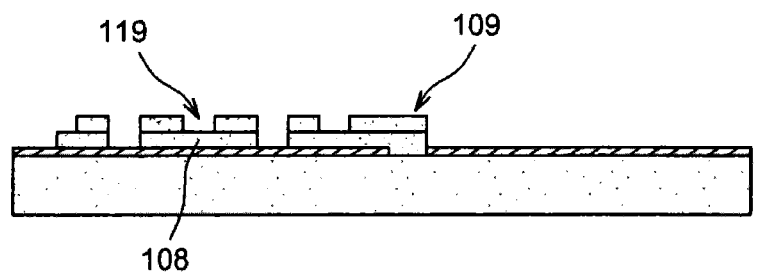

Next a sacrificial masking 109 is formed on the layer of dielectric material 108, comprising holes 119 revealing the dielectric material 108 (FIG. 8B). The sacrificial masking 109 may for example be based on photosensitive resin, or a dielectric material deposited for example by screen printing or by inkjet.

Figure 8C:
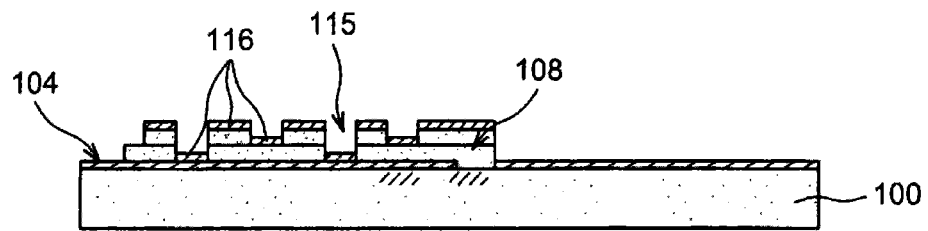

Next a deposition is effected of a metal layer 116, for example based on Au or Pt or Ag or Ti, with a thickness that may for example be between 30 nm and several hundreds of nanometers. The metallic layer 116 is formed at the bottom of the holes 119 passing through the sacrificial masking layer 109, as well as at the bottom of the holes 115 produced in the dielectric layer 108, the regions of the dielectric layer 108 protected by the sacrificial masking 109 for their part not being covered by this metallic layer 116 (FIG. 8C).

Figure 8D:
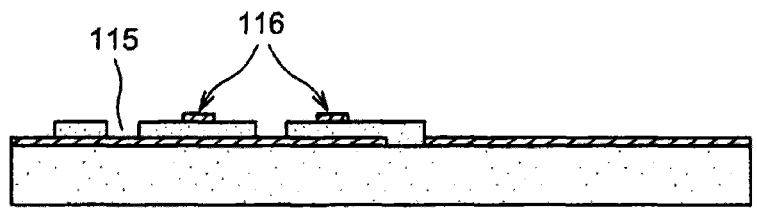

Next the sacrificial masking layer 109 is removed (FIG. 8D).

In order to effect this removal when the sacrificial layer is based on resin, it can be dissolved in a solvent, for example based on acetone. This sacrificial masking layer may also optionally be removed by means of a suitable plasma.

Next the second electrode 114 is formed on the dielectric region 108, for example by deposition of a conductive layer 112 of graphene by screen printing.

Figure 8E:
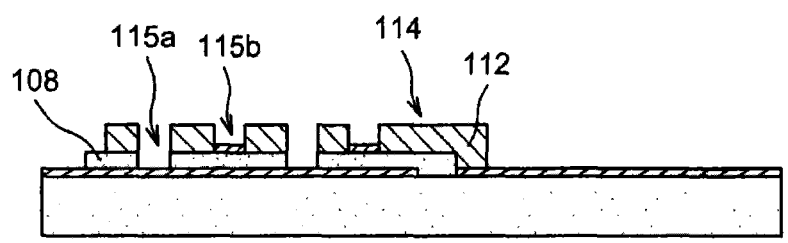

This conductive layer 112 may optionally be formed with holes. The conductive layer 112 may be provided with holes 115a passing through the graphene layer and situated in line with those formed in the dielectric layer 108, as well as holes 115b revealing the metal regions 107 formed on the dielectric layer 108 (FIG. 8E).

Then the hydrophobic protective layer 120 covering the second electrode 114 is formed.

Figure 8F:
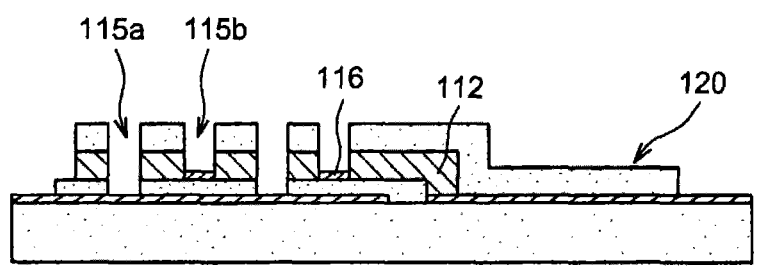

This protective layer 120 comprises openings 125 in line with the holes 115b passing through the graphene layer and holes 115a passing through both the graphene layer and the layer of dielectric material 108 (FIG. 8F).

Next a hydrophilic polar SAM layer 107 is formed at the bottom of the holes revealing the first electrode 104 and the holes revealing the metal layer 116 resting on the dielectric layer 107 (FIG. 8G). The hydrophilic polar SAM layer may be produced by dipping or evaporation.

A humidity sensor as implemented according to the invention may also be provided in a temperature-measurement device in order to make a temperature measurement by measuring a variation in capacitance.

To make the sensor more sensitive to variations in temperature, a metal material 212 can be deposited on the layer of conductive material 112 forming the top electrode 114 of the sensor. This metal material 212 can be intended to be diffused inside the conductive material 112.

Figure 9:
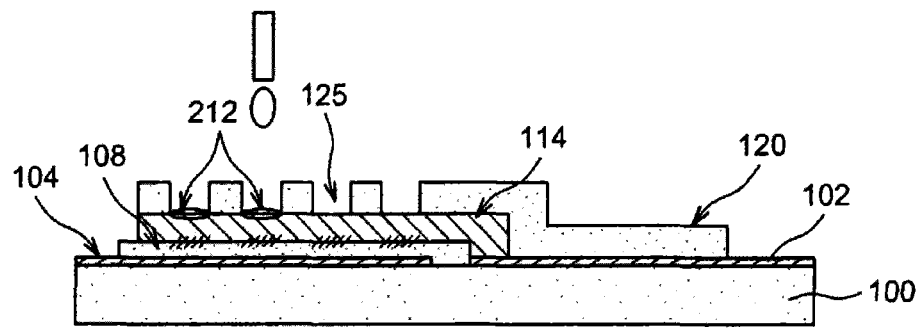
FIG. 9 illustrates an example of treatment for making the capacitive-type humidity sensor according to the invention sensitive to variations in temperature.

In the case where the conductive material 112 forming the top electrode 114 is graphene, the metal material 212 may for example be silver deposited in the form of drops, for example by inkjet, through the openings 125 in the protective layer 120 (FIG. 9). Adding metal particles such as silver particles in the graphene increasing its TCR coefficient (temperature coefficient of resistivity), which corresponds to a resistivity change factor per degree of temperature.

Figure 10:
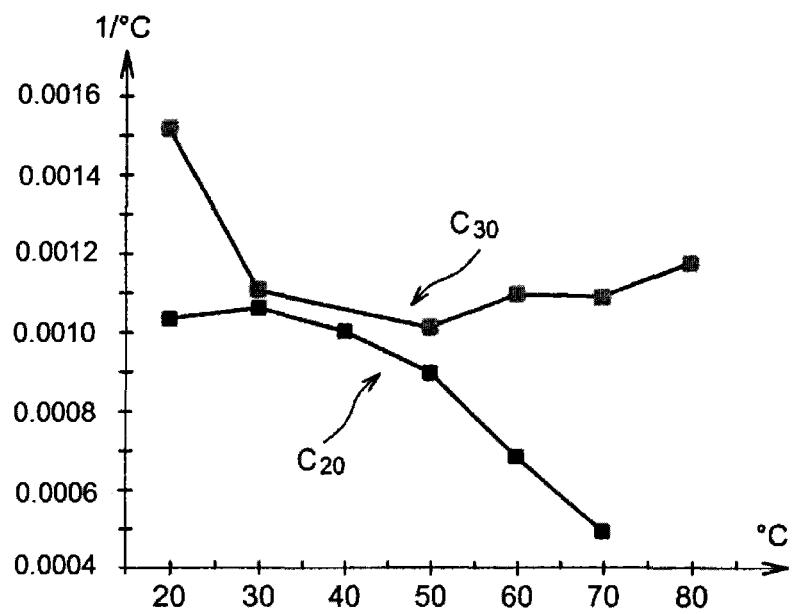
FIG. 10 illustrates the effect on its TCR coefficient of an addition of Ag particles on a material consisting of graphene.

In FIG. 10, curves $C_{20}$, $C_{30}$ illustrate variations in TCR coefficient respectively of an element consisting of graphene and an element based on a material consisting of graphene and particles of Ag of around 25% by weight.

The invention claimed is:

1. A humidity sensor comprising, on a support:
a first electrode disposed on a surface of the support;
a region of dielectric material disposed on a surface of the first electrode, the region of dielectric material being impermeable to moisture; and
a second electrode comprising a layer of conductive material and disposed on a surface of the region of dielectric material, the second electrode having a permeability to moisture greater than a permeability to moisture of the region of dielectric material,
wherein the first electrode is in direct contact with the region of the dielectric material, and
wherein the first electrode, the region of dielectric material, and the second electrode form a capacitor having a capacitance that varies based on a level of moisture at an interface between the second electrode and the region of dielectric material.

2. The humidity sensor according to claim 1, wherein the region of dielectric material is non-porous or comprises pores with a maximum dimension of 4 nm and/or a maximum porosity ratio of less than 8%.

3. The humidity sensor according to claim 1, wherein the dielectric material is hydrophobic.

4. The humidity sensor according to claim 1, wherein the second electrode is covered with a perforated hydrophobic protective layer.

5. A humidity sensor comprising, on a support:
a first electrode disposed on a surface of the support;
a region of dielectric material disposed on a surface of the first electrode, the region of dielectric material being impermeable to moisture; and
a second electrode comprising a layer of conductive material and disposed on a surface of the region of dielectric material, the second electrode having a permeability to moisture greater than a permeability to moisture of the region of dielectric material,
wherein the second electrode is a graphene electrode, and
wherein the first electrode, the region of dielectric material, and the second electrode form a capacitor having a capacitance that varies based on a level of moisture at an interface between the second electrode and the region of dielectric material.

6. A humidity sensor comprising, on a support:
a first electrode disposed on a surface of the support;
a region of dielectric material disposed on a surface of the first electrode, the region of dielectric material being impermeable to moisture; and
a second electrode comprising a layer of conductive material and disposed on a surface of the region of dielectric material, the second electrode having a permeability to moisture greater than a permeability to moisture of the region of dielectric material,
wherein holes pass through the second electrode, and
wherein the first electrode, the region of dielectric material, and the second electrode form a capacitor having a capacitance that varies based on a level of moisture at an interface between the second electrode and the region of dielectric material.

7. The humidity sensor according to claim 6, wherein at least one hole among the holes also passes through the region of dielectric material and reveals the first electrode.

8. The humidity sensor according to claim 7, wherein at least one hole reveals a hydrophilic self-assembled monolayer on the first electrode.

9. The humidity sensor according to claim 7, wherein at least one hole reveals a hydrophilic self-assembled monolayer on the second electrode.

10. The humidity sensor according to claim 6, comprising in alternation holes revealing the first electrode and holes revealing the second electrode.

11. The humidity sensor according to claim 10, wherein at least one hole reveals a hydrophilic self-assembled monolayer on the first electrode.

12. The humidity sensor according to claim 10, wherein at least one hole reveals a hydrophilic self-assembled monolayer on the second electrode.

* * * * *